(12) United States Patent
Chiang

(10) Patent No.: US 12,408,953 B2
(45) Date of Patent: Sep. 9, 2025

(54) SPINAL LAMINA PROTECTOR

(71) Applicant: Orion Biotech Inc., Taipei (TW)

(72) Inventor: Ming-Fu Chiang, Taipei (TW)

(73) Assignee: NEUCEN BIOMED CO., LTD., Taipei (TW)

( * ) Notice: Subject to any disclaimer, the term of this patent is extended or adjusted under 35 U.S.C. 154(b) by 312 days.

(21) Appl. No.: 18/144,844

(22) Filed: May 8, 2023

(65) Prior Publication Data
US 2024/0374295 A1 Nov. 14, 2024

(51) Int. Cl.
*A61B 17/70* (2006.01)
(52) U.S. Cl.
CPC ........ *A61B 17/7071* (2013.01); *A61B 17/707* (2013.01)
(58) Field of Classification Search
CPC .............. A61B 17/707; A61B 17/7071; A61B 17/8004; A61B 17/8023
See application file for complete search history.

(56) References Cited

U.S. PATENT DOCUMENTS

| | | | | | |
|---|---|---|---|---|---|
| 2,406,832 | A | * | 9/1946 | Hardinge | A61B 17/8009 606/71 |
| 2,486,303 | A | * | 10/1949 | Longfellow | A61B 17/80 606/71 |
| 5,616,142 | A | * | 4/1997 | Yuan | A61F 2/2846 606/71 |
| 6,306,136 | B1 | * | 10/2001 | Baccelli | A61B 90/92 606/279 |
| 7,318,825 | B2 | * | 1/2008 | Butler | A61B 17/8047 606/71 |
| 7,331,961 | B2 | * | 2/2008 | Abdou | A61B 17/8004 606/71 |
| 7,635,366 | B2 | * | 12/2009 | Abdou | A61B 17/8023 606/71 |
| 7,727,265 | B2 | * | 6/2010 | Paul | A61B 17/7059 606/295 |
| 2008/0269904 | A1 | | 10/2008 | Voorhies | |
| 2009/0076509 | A1 | * | 3/2009 | Bush, Jr. | A61B 17/88 606/280 |
| 2010/0174315 | A1 | * | 7/2010 | Scodary | A61B 17/7052 606/264 |

(Continued)

FOREIGN PATENT DOCUMENTS

CN 105055057 A 11/2015
CN 107530110 A 1/2018

(Continued)

*Primary Examiner* — Nicholas W Woodall
(74) *Attorney, Agent, or Firm* — Cheng-Ju Chiang

(57) ABSTRACT

The invention discloses a spinal lamina protector. The spinal lamina protector comprises a first protection part and a second protection part. Specifically, the first protection part comprises a first engaging portion, a first holding portion and a supporting portion, and the supporting portion and the first holding portion form an engaging rail. The engaging rail makes a second engaging portion of the second protection part insert in, and a second holding portion of the second protection part holds the first engaging portion while the second engaging portion is in the engaging rail. Therefore, the abovementioned structure of the spinal lamina protector forms a stable and length-adjustable structure, even if a pressure is pressed on the spinal lamina protector.

10 Claims, 9 Drawing Sheets

(56) References Cited

U.S. PATENT DOCUMENTS

2012/0158060 A1* 6/2012 Abrahams .......... A61B 17/7065
   606/252
2016/0095712 A1 4/2016 Faulhaber

FOREIGN PATENT DOCUMENTS

CN 112807070 A 5/2021
TW 202210039 A 3/2022

* cited by examiner

SPINAL LAMINA PROTECTOR

TECHNICAL FIELD

The present invention relates to a spinal lamina protector which is designed to perform a stable and length-adjustable structure and for protecting the spinal cord from adhesion and external pressure after implanted in human body.

BACKGROUND OF RELATED ARTS

The lamina is a posterior arch of the vertebral bone lying between the spinous process and the lateral pedicles with the transverse processes of each vertebra. The pair of laminae, along with the spinous process, make up the posterior wall of the bony spinal canal. However, some diseases may cause the bony spinal canal narrowed and pressing the spinal nerves, e.g. spinal stenosis.

Most commonly, a laminectomy is performed to treat spinal stenosis. Spinal stenosis is the single most common disease that leads to spinal surgery, of which a laminectomy represents one component. The lamina of the vertebra is removed or trimmed to widen the spinal canal and create more space for the spinal nerves and thecal sac.

A laminectomy can treat severe spinal stenosis by relieving pressure on the spinal cord. After this surgery, part of the spinal cord which is originally protected by the lamina may directly contact to the surrounding tissue due to the laminae per se have been removed. This change might cause potential scar tissue or fibrosis problems to spinal cord after laminectomy.

Therefore, a device for keeping the spinal cord protected as the laminae could help to prevent the abovementioned problems. The device is to instead the removed lamina after laminectomy. To meet the different vertebra size and different laminectomy situation, the protective device is better to be length-adjustable.

To achieve the adjustable characteristic, the protective device is designed with two or more components assembled. For medical device like this, the stability is most important. Hence, to design a protective device both stable and adjustable is an important issue nowadays.

SUMMARY

To resolve the drawbacks of the prior arts, the present invention discloses a spinal lamina protector which includes a first protection part and a second protection part. The second protection part is detachably connected with the first protection part.

Furthermore, the first protection part comprises a top plate, a first engaging portion, a first holding portion, a supporting portion and a first fixing portion. The first engaging portion is configured on the top plate, and the first holding portion is configured on the top plate, too. Thereafter, the supporting portion is configured beside the top plate, and the first fixing portion is connected with the top plate and the supporting portion simultaneously. Specifically, the supporting portion and the first holding portion form an engaging rail.

On the other hand, the second protection part comprises a lower plate, an overlapping portion, a second engaging portion, a second holding portion and a second fixing portion. The overlapping portion is configured beside the lower plate. The second engaging portion is configured on the overlapping portion, and the second holding portion is configured on the overlapping portion, too. Moreover, the second fixing portion is connected with the lower plate and the overlapping portion simultaneously.

In present invention, the second engaging portion firstly engages with the first engaging portion, making the second engaging portion insert into the engaging rail, and the second engaging portion slides in the engaging rail until the first holding portion contacts the second holding portion.

Embodiments of the invention are illustrated by way of example, and not by way of limitation, in the figures of the accompanying drawings in which like reference numerals refer to similar elements.

DETAILED DESCRIPTION OF THE INVENTION

In order to understand the technical features and practical efficacy of the present invention and to implement it in accordance with the contents of the specification, hereinafter, preferred embodiments of the present invention will be described in detail with reference to the accompanying drawings.

Figure 1:
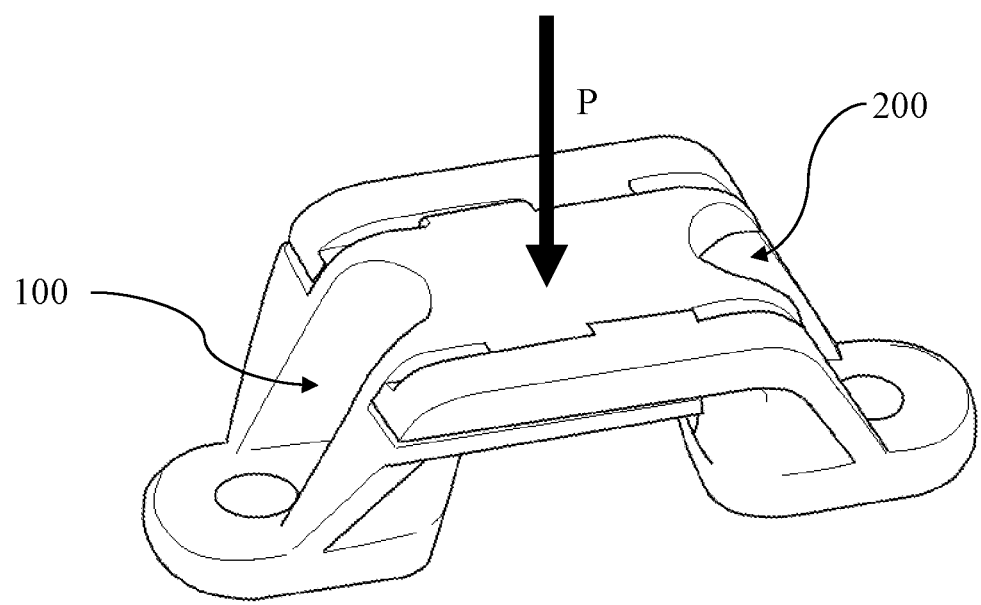
FIG. 1 is a schematic drawing of the embodiment of the present invention.
Figure 2:
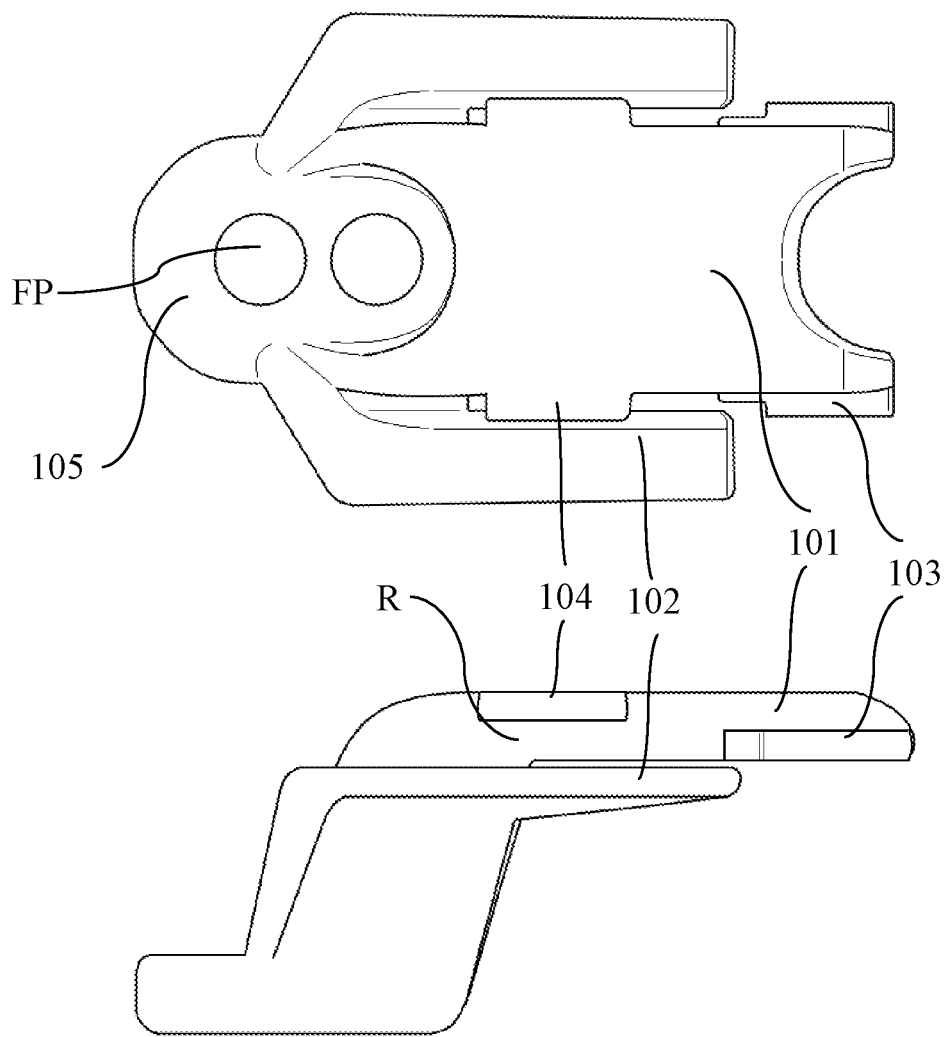
FIG. 2 is a schematic drawing of the first protection part of the embodiment of the present invention.
Figure 3:
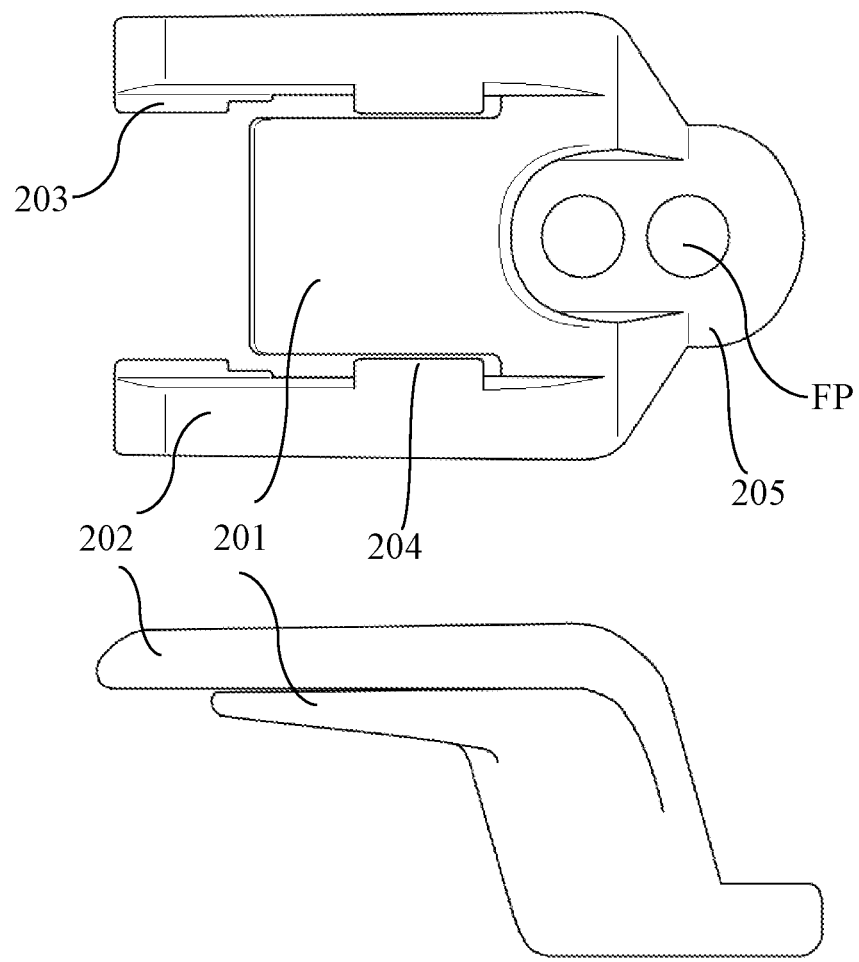
FIG. 3 is a schematic drawing of the second protection part of the embodiment of the present invention.

Please refer to FIG. 1, FIG. 2 and FIG. 3 simultaneously. FIG. 1 is a schematic drawing of the embodiment of the present invention. FIG. 2 is a schematic drawing of the first protection part of the embodiment of the present invention. FIG. 3 is a schematic drawing of the second protection part of the embodiment of the present invention.

First of all, FIG. 1 illustrates the spinal lamina protector 10 of the present embodiment. Specifically, the spinal lamina protector 10 of the present embodiment is arch shaped, and the spinal lamina protector 10 comprises a first protection part 100 and a second protection part 200. The second protection part 200 is detachably connected with the first protection part 100. The spinal lamina protector 10 with specific structure may bear the pressure P thus to protect the spinal cord.

Please refer to FIG. 2. FIG. 2 illustrates the top view and the side view of the first protection part 100 of the present embodiment. The first protection part 100 comprises top plate 101, first engaging portion 103, first holding portion 104, supporting portion 102 and first fixing portion 105. The first engaging portion 103 is configured on the top plate 101, and the first holding portion 104 is configured on the top plate 101, too.

On the other hand, the supporting portion 102 is configured beside the top plate 101, and the first fixing portion 105 is connected with the top plate 101 and the supporting portion 102 simultaneously. Moreover, the supporting portion 102 and the first holding portion 104 form an engaging rail R.

In present embodiment, the number of supporting portion 102 and first engaging portions 103 are two. Two supporting portions 102 are configured on but not contact both sides of the top plate 101. Furthermore, two first engaging portions 103 are directly configured on both ending sides of the top plate 101. The end of the top plate 101 is designed to form an arch shaped notch, therefore to accommodate the terminal shape of the lower plate 201. The first fixing portion 105 of the present embodiment is deposed at a lower place related to the top plate 101, thus the first protection part 100 forms a structure which is similar to letter "Z", and so do the lower plate 201, overlapping portion 202 and second fixing portion 205 of the second protection part 200.

In this embodiment, two fixing pores FP are configured on the first fixing portion 105, and so does the second fixing portion 205. The number of the fixing pores FP may increase the adjustment ability of the first fixing portion 105 and second fixing portion 205.

Please refer to FIG. 3. FIG. 3 illustrates the top view and the side view of the second protection part 200 of the present embodiment. the second protection part 200 of the present embodiment comprises lower plate 201, overlapping portion 202, a second engaging portion 203, a second holding portion 204 and a second fixing portion 205. The overlapping portion 202 is configured beside the lower plate 201. The second engaging portion 203 is configured on the overlapping portion 202, and the second holding portion 204 is configured on the overlapping portion, too. Moreover, the second fixing portion 205 is connected with the lower plate 202 and the overlapping portion 202 simultaneously.

In this embodiment, the number of the overlapping portion 202 and second engaging portion 203 are two. The overlapping portions 202 are configured on but not contact the lower plate 201. On the other hand, two second engaging portions 203 are respectively configured on the end of overlapping portion 202. The purpose of the configuration of the overlapping portion 202 is to overlap the supporting portion 102 illustrated in FIG. 2, and the second engaging portion 203 is designed to be inserted and slides in the aforementioned engaging rail R therein.

In other words, the second engaging portion 203 firstly engages with the first engaging portion 103, making the second engaging portion 203 insert into the engaging rail R, and the second engaging portion 203 slides in the engaging rail R until the first holding portion 104 contacts the second holding portion 204.

Figure 4:
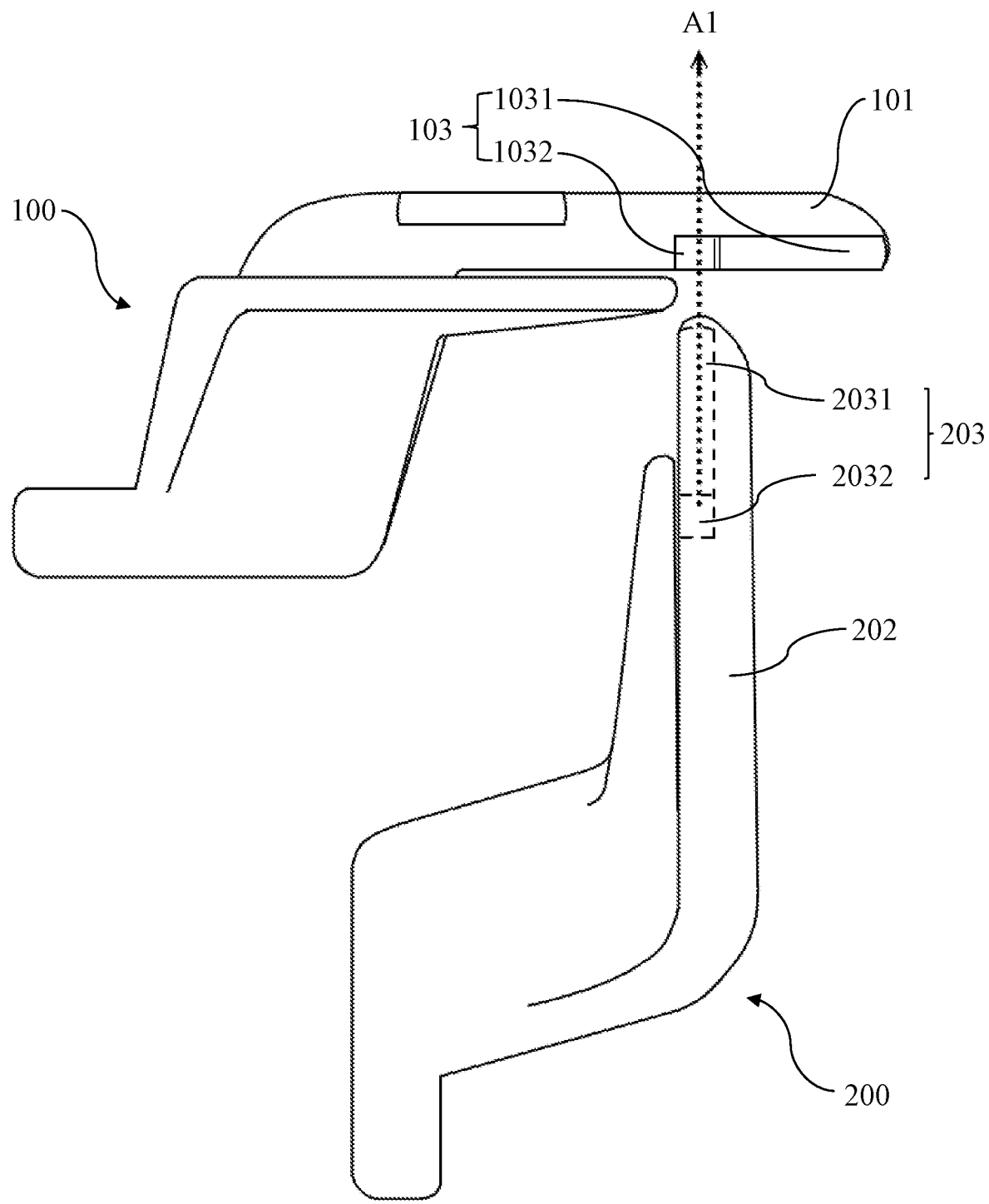
FIG. 4 is a schematic drawing of latching mechanism of the embodiment of the present invention.
Figure 5:
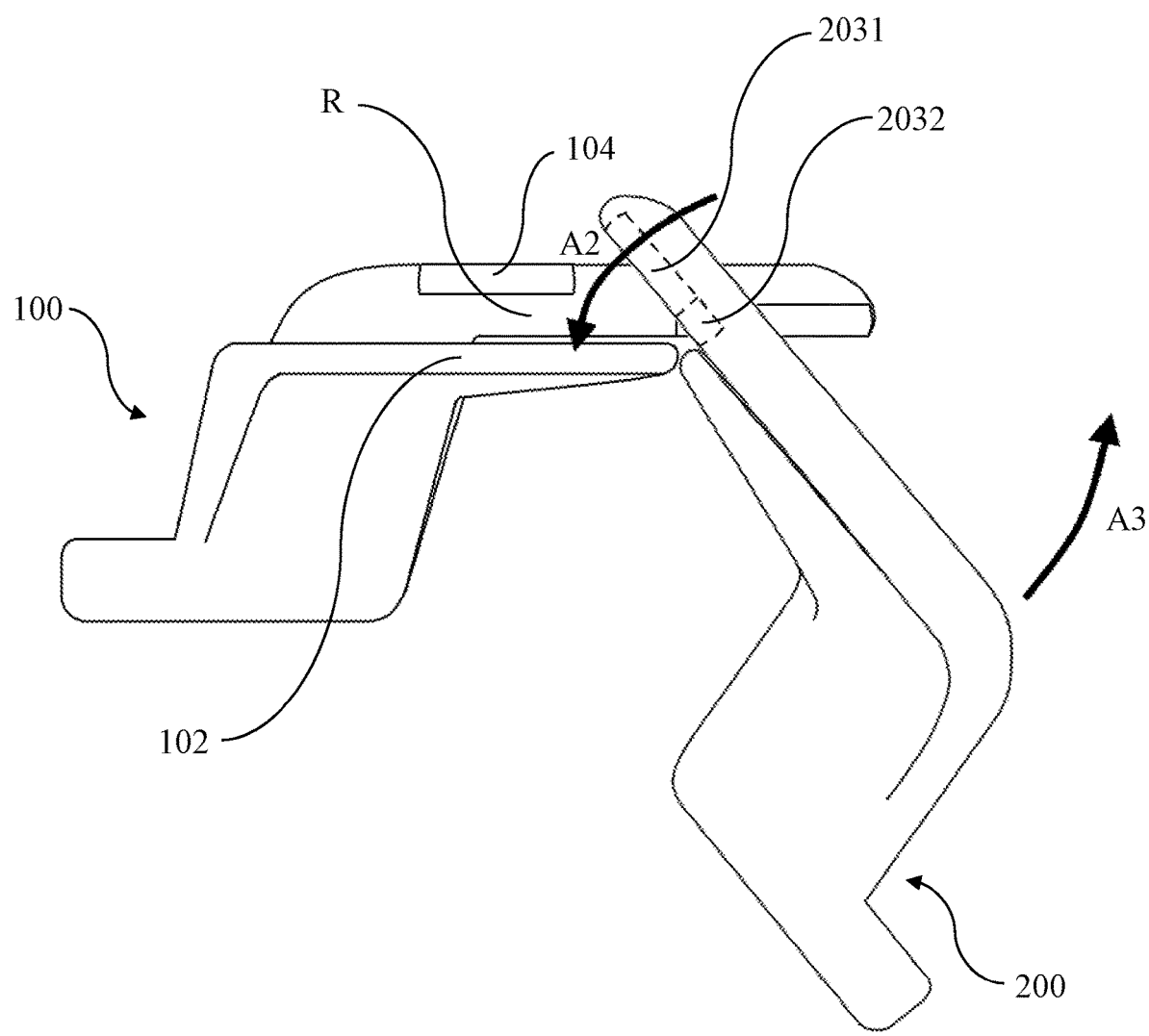
FIG. 5 is the other schematic drawing of latching mechanism of the embodiment of the present invention.
Figure 6:
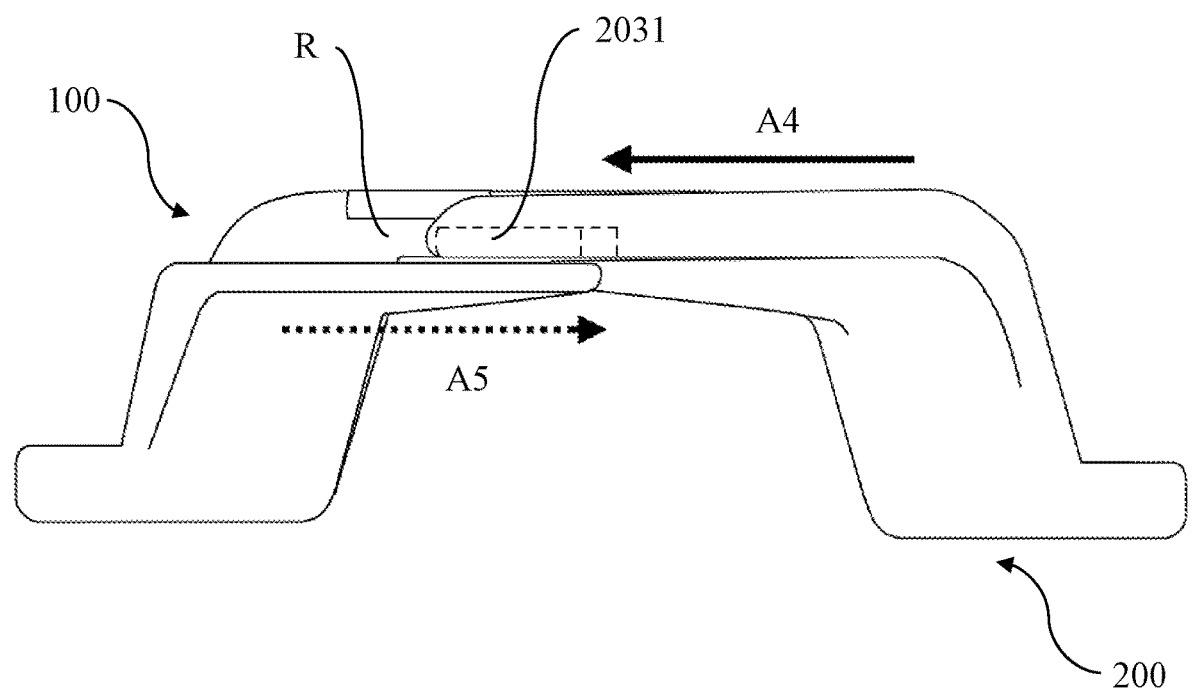
FIG. 6 is a schematic drawing of engaging rail of the embodiment of the present invention.
Figure 7:
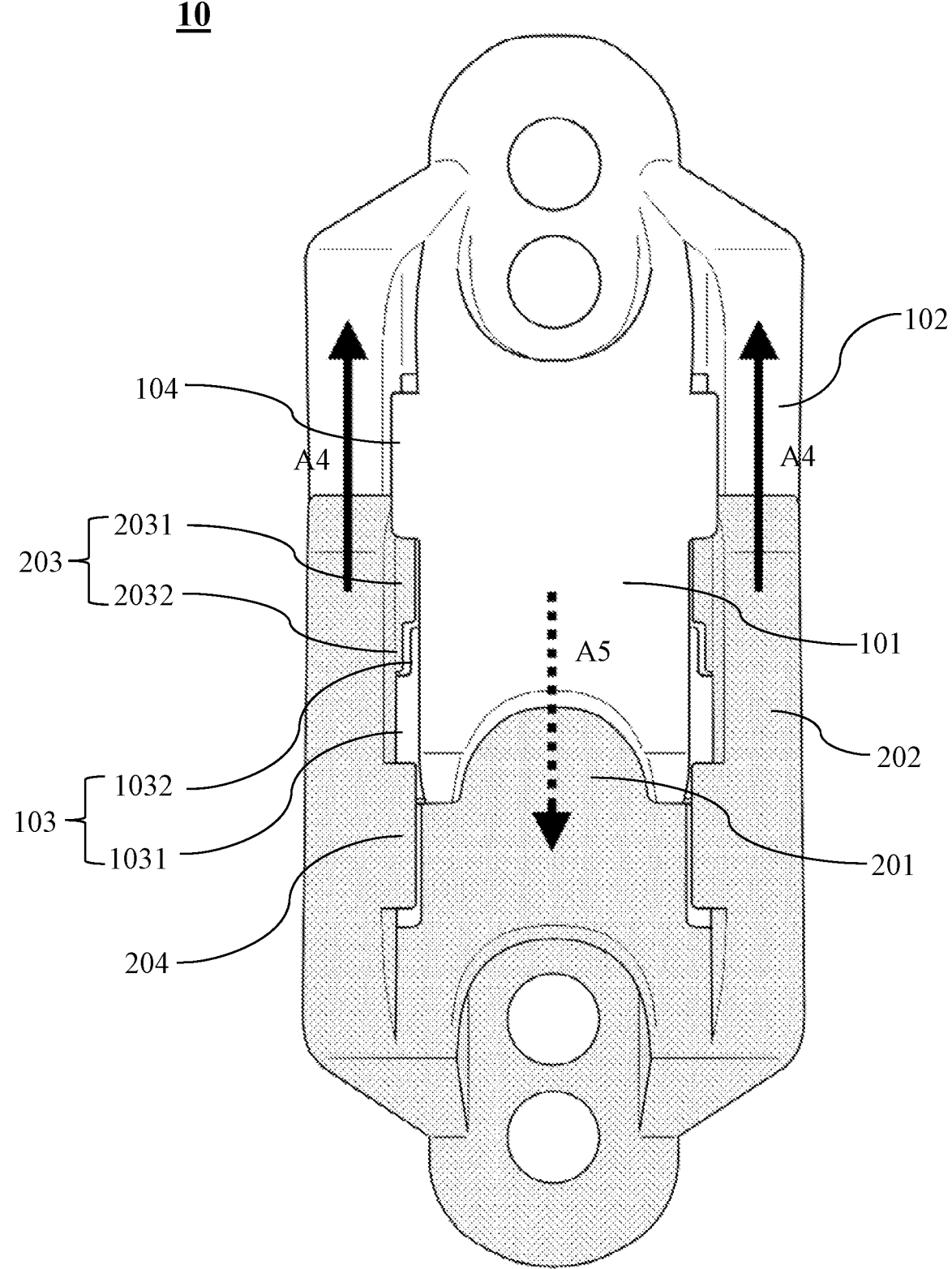
FIG. 7 is a top view drawing of FIG. 6.

In light of the specific way of creating connection between the first protection part 100 and a second protection part 200, please refer to FIG. 4 to FIG. 7 simultaneously. FIG. 4 is a schematic drawing of latching mechanism of the embodiment of the present invention. FIG. 5 is the other schematic drawing of latching mechanism of the embodiment of the present invention. FIG. 6 is a schematic drawing of engaging rail of the embodiment of the present invention, and FIG. 7 is a top view drawing of FIG. 6.

As shown in FIG. 4, this figure obviously shows that the first engaging portion 103 of the present embodiment comprises a first rib 1031 and a first notch 1032, and the second engaging portion 203 comprises a second rib 2031 and a second notch 2032. In this embodiment, the first rib 1031 and first notch 1032 form an L-shaped structure and so do second rib 2031 and second notch 2032. When the first engaging portion 103 has been ready for engaging with the second engaging portion 203, the second rib 2031 may be aligned with the first notch 1032 at first.

Thereinafter, the second rib 2031 contacts and goes through the first notch 1032 along with the direction of dotted line arrow A1. In FIG. 4, the aforementioned "goes through" is like a latch. In other words, pair of the overlapping portion 202 may be transiently bended in different direction and the distance therebetween two overlapping portions 202 may be enlarged while the second rib 2031 is going through the first notch 1032, until the first notch 1032 contacts the second notch 2032.

Please refer to FIG. 5, after the first notch 1032 contacts the second notch 2032, the second protection part 200 will be rotated as the directions shown by arrow A2 and arrow A3. In this step, the purpose of the present embodiment is to make the second rib 2031 insert into the engaging rail R. Please notice that the end point of first holding portion 104 needs to be designed on the route of second rib 2031 while the second rib 2031 is rotated along with the direction of arrow A2. This mechanism may create a transient stopper which is played by first holding portion 104 and make the first holding portion 104 successfully holds the second rib 2031 after the second rib 2031 has been inserted into the engaging rail R.

After the second rib 2031 has been inserted into the engaging rail R, as shown in FIG. 6, the first rib 1031 will be inserted into the engaging rail R, too. Otherwise, the first rib 1031 and the second rib 2031 are able to slide in the engaging rail R, thus the first protection part 100 will slides along the direction of dotted line arrow A5 and the second protection part 200 will slides along the direction of arrow A4.

In FIG. 6, the dotted line arrow A5 and the arrow A4 further show how to adjust the length of the spinal lamina protector 10. That is, the first holding portion 104 and the second holding portion 204 linearly moves in the same line and so do the first engaging portion 103 and the second engaging portion 203.

When the spinal lamina protector 10 extends the length to the extreme limit per se, the first holding portion 104 contact against the second holding portion 204, and the L-shaped first rib 1031 and first notch 1032 contact against the L-shaped seconds rib 2031 and second notch 2032, too. On the other hand, the first holding portion 104 always holds the seconds rib 2031 and second notch 2032 from the top, and the second holding portion 204 always holds the first rib 1031 and first notch 1032 from the top, too.

Moreover, to more clearly point out the mechanism which works in the present embodiment, the second protection part 200 is shaded in FIG. 7. Therefore, FIG. 7 further illustrates that the top plate 101 slides on the upper surface of lower plate 201, and the overlapping portion 202 slides on the upper surface of supporting portion 102 in the present embodiment.

The abovementioned mechanism may not only design the adjustable length range of the spinal lamina protector 10, but also make the spinal lamina protector 10 become more stable. Please refer to FIG. 8, FIG. 8 is a schematic drawing illustrating how the first holding portion and the second holding portion work of the embodiment of the present invention.

Figure 8:
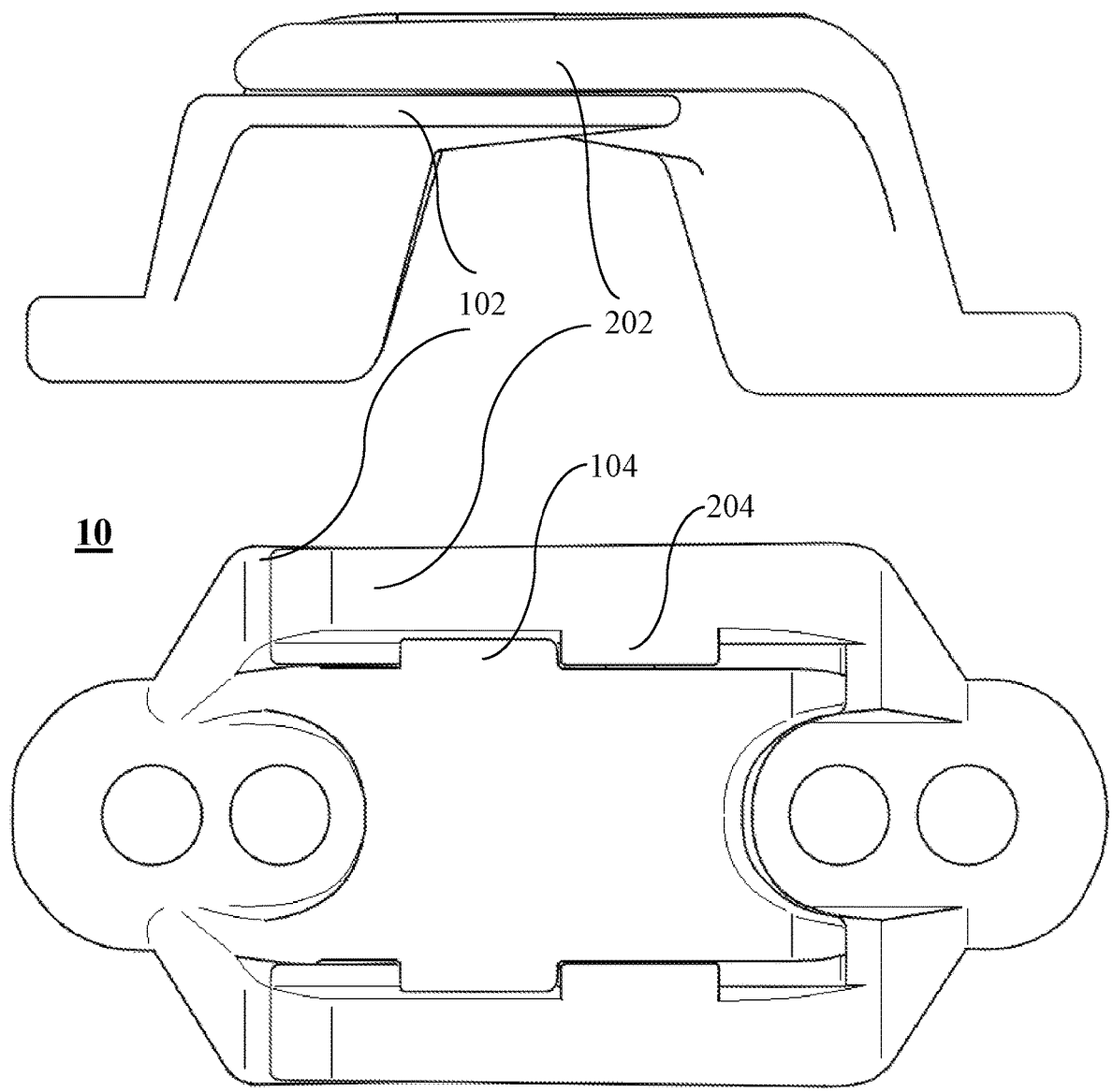
FIG. 8 is a schematic drawing illustrating how the first holding portion and the second holding portion work of the embodiment of the present invention.

As shown in FIG. 7 and FIG. 8, the reason why the spinal lamina protector 10 of the present embodiment becomes more stable is that the first holding portion 104 restricts the rotation of the second engaging portion 203 from the top and the second holding portion 204 restricts the rotation of the first engaging portion 103 while the first engaging portion 103 and the second engaging portion 203 are inserting into the engaging rail R. Therefore, the first engaging portion 103, the second engaging portion 203, the first holding portion 104, and the second holding portion 204 form double levers against each other, creating a specific and stable structure of spinal lamina protector 10 for bearing the pressure P.

Figure 9:
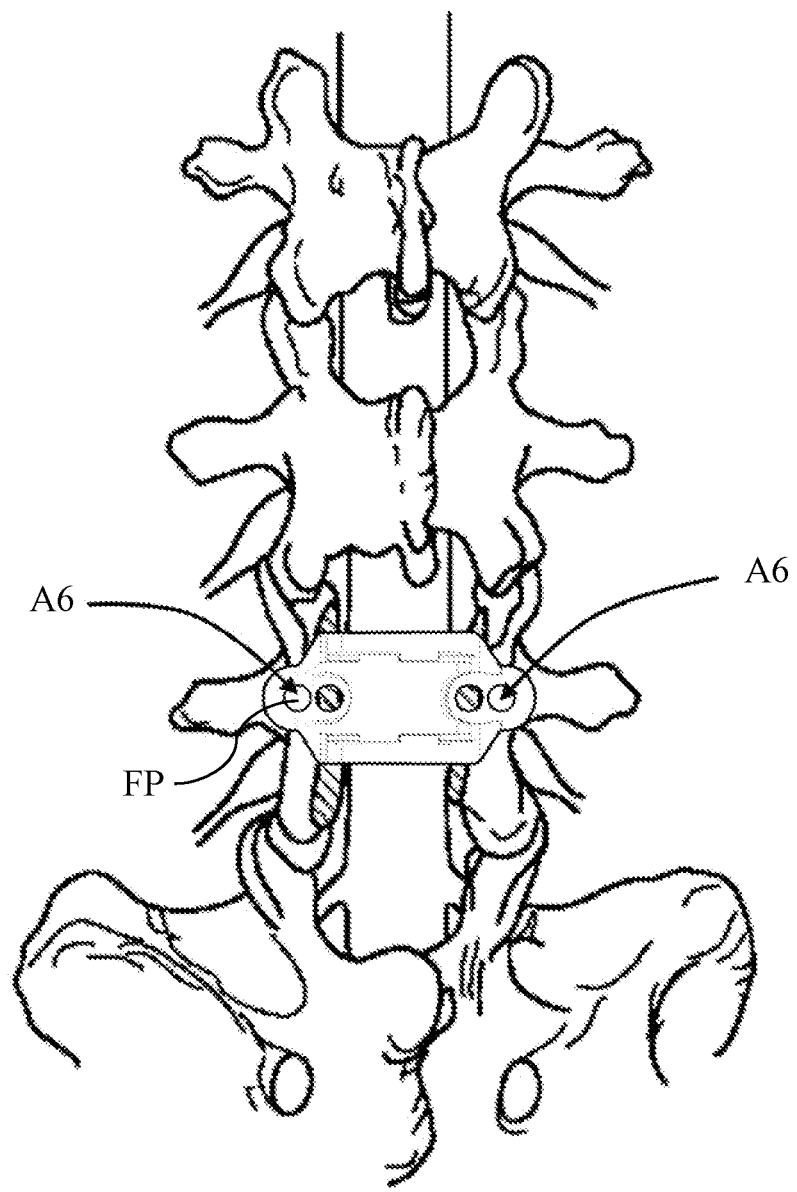
FIG. 9 is a schematic drawing of the first fixing portion and the second fixing portion of the embodiment of the present invention.

Please refer to FIG. 9, FIG. 9 is a schematic drawing of the first fixing portion and the second fixing portion of the embodiment of the present invention. FIG. 9 shows the installation method of the spinal lamina protector 10 of the present embodiment. Fasteners such as nails or pins may be used for fixing the length adjusted spinal lamina protector 10 via the fixing pore FP along with the direction of arrow A6 on the vertebra after laminectomy, thus to form the above-mentioned double lever structure.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure. While the preferred embodiment of the invention has been illustrated and described, it will be appreciated that various changes can be made therein without departing from the spirit and scope of the invention.

What is claimed:

1. A spinal lamina protector, comprising:
    a first protection part, comprising:
        a top plate;
        a first engaging portion, configured on the top plate;
        a first holding portion, configured on the top plate;
        a supporting portion, configured beside the top plate;
        a first fixing portion, connected with the top plate and the supporting portion simultaneously;
        wherein the supporting portion and the first holding portion form an engaging rail;
    a second protection part, detachably connected with the first protection part, wherein the second protection part comprises:
        a lower plate;
        an overlapping portion, configured beside the lower plate;
        a second engaging portion, configured on the overlapping portion;
        a second holding portion, configured on the overlapping portion;
        a second fixing portion, connected with the lower plate and the overlapping portion simultaneously;
    wherein the second engaging portion firstly engages with the first engaging portion, making the second engaging portion insert into the engaging rail, and the second engaging portion slides in the engaging rail until the first holding portion contacts the second holding portion.

2. The spinal lamina protector as claimed in claim 1, wherein the first engaging portion further comprises a first rib and a first notch.

3. The spinal lamina protector as claimed in claim 1, wherein the second engaging portion further comprises a second rib and a second notch.

4. The spinal lamina protector as claimed in claim 2, wherein the second holding portion restricts rotation of the first engaging portion while first engaging portion is inserting into the engaging rail.

5. The spinal lamina protector as claimed in claim 3, wherein the first holding portion restricts rotation of the second engaging portion while the second engaging portion is inserting into the engaging rail.

6. The spinal lamina protector as claimed in claim 1, wherein the top plate slides on the lower plate.

7. The spinal lamina protector as claimed in claim 1, wherein the overlapping portion slides on the supporting portion.

8. The spinal lamina protector as claimed in claim 1, wherein the spinal lamina protector is arch shaped.

9. The spinal lamina protector as claimed in claim 1, wherein the first fixing portion further comprises at least one fixing pore.

10. The spinal lamina protector as claimed in claim 1, wherein the second fixing portion further comprises at least one fixing pore.

* * * * *